US011837368B1

(12) United States Patent
Helton et al.

(10) Patent No.: US 11,837,368 B1
(45) Date of Patent: Dec. 5, 2023

(54) MULTI-CHANNEL COMMUNICATION SESSIONS BETWEEN PATIENT AND CLINICIAN

(71) Applicant: Amazon Technologies, Inc., Seattle, WA (US)

(72) Inventors: Kristen Lloyd Helton, Seattle, WA (US); Alexander Davidson, Seattle, WA (US); Benjamin Green, Seattle, WA (US); Patrick Denton, Seattle, WA (US)

(73) Assignee: Amazon Technologies, Inc., Seattle, WA (US)

( * ) Notice: Subject to any disclaimer, the term of this patent is extended or adjusted under 35 U.S.C. 154(b) by 319 days.

(21) Appl. No.: 16/814,937

(22) Filed: Mar. 10, 2020

(51) Int. Cl.
| | |
|---|---|
| *G06Q 50/22* | (2018.01) |
| *G06Q 30/00* | (2023.01) |
| *G16H 80/00* | (2018.01) |
| *G16H 30/40* | (2018.01) |
| *H04N 21/2385* | (2011.01) |
| *H04M 3/56* | (2006.01) |
| *G16H 15/00* | (2018.01) |
| *H04L 67/12* | (2022.01) |
| *H04L 65/403* | (2022.01) |
| *H04L 65/401* | (2022.01) |

(52) U.S. Cl.
CPC ............ *G16H 80/00* (2018.01); *G16H 15/00* (2018.01); *G16H 30/40* (2018.01); *H04L 65/403* (2013.01); *H04L 65/4015* (2013.01); *H04L 67/12* (2013.01); *H04M 3/567* (2013.01); *H04N 21/2385* (2013.01)

(58) Field of Classification Search
CPC . H04L 67/42; H04L 41/0859; H04L 67/1095; H04L 67/34; G06F 8/61
See application file for complete search history.

(56) References Cited

U.S. PATENT DOCUMENTS

| | | | |
|---|---|---|---|
| 2011/0191356 A1* | 8/2011 | Gazula | G16H 30/40 707/752 |
| 2013/0246084 A1* | 9/2013 | Parmanto | G06Q 10/06 705/2 |
| 2016/0323324 A1* | 11/2016 | Knotts | H04L 65/104 |
| 2018/0060535 A1* | 3/2018 | Reicher | G16H 50/30 |
| 2019/0180862 A1* | 6/2019 | Wisser | G16H 80/00 |
| 2019/0313252 A1* | 10/2019 | Ting | H04W 76/10 |
| 2020/0066414 A1* | 2/2020 | Neff | H04L 12/1818 |

* cited by examiner

*Primary Examiner* — Christopher B Robinson
(74) *Attorney, Agent, or Firm* — Athorus, PLLC

(57) ABSTRACT

Described are systems and methods directed to a multi-channel communication system that enables real-time or near real-time communication between two or more individuals, such as a patient and a clinician in which at least one of the individuals uses one device for audio/video communication and another device for exchange of data, such as annotated images. For example, a patient may utilize a patient device to communicate with a clinician via a first clinician device. In addition to the first clinician device, the clinician may also use a second clinician device to annotate and share visual data, such as templates or patient images, with the patient, without disrupting the audio/video communication between the patient device and the first clinician device.

21 Claims, 9 Drawing Sheets

MULTI-CHANNEL COMMUNICATION SESSIONS BETWEEN PATIENT AND CLINICIAN

BACKGROUND

Content, businesses, communication, etc., continues to move to a network-based method, with data being shared between devices of the network, meetings between individuals and business occurring over network communications (e.g., video conferences), etc. Many existing video conference systems allow users to view on their respective device live video streams of each participant during a meeting, share screens of the device connected to the video conference, etc. In each such system, each participant connects via a single device and each participant sees and hears everything that occurs during the meeting on their connected device.

DETAILED DESCRIPTION

Figure 1A:
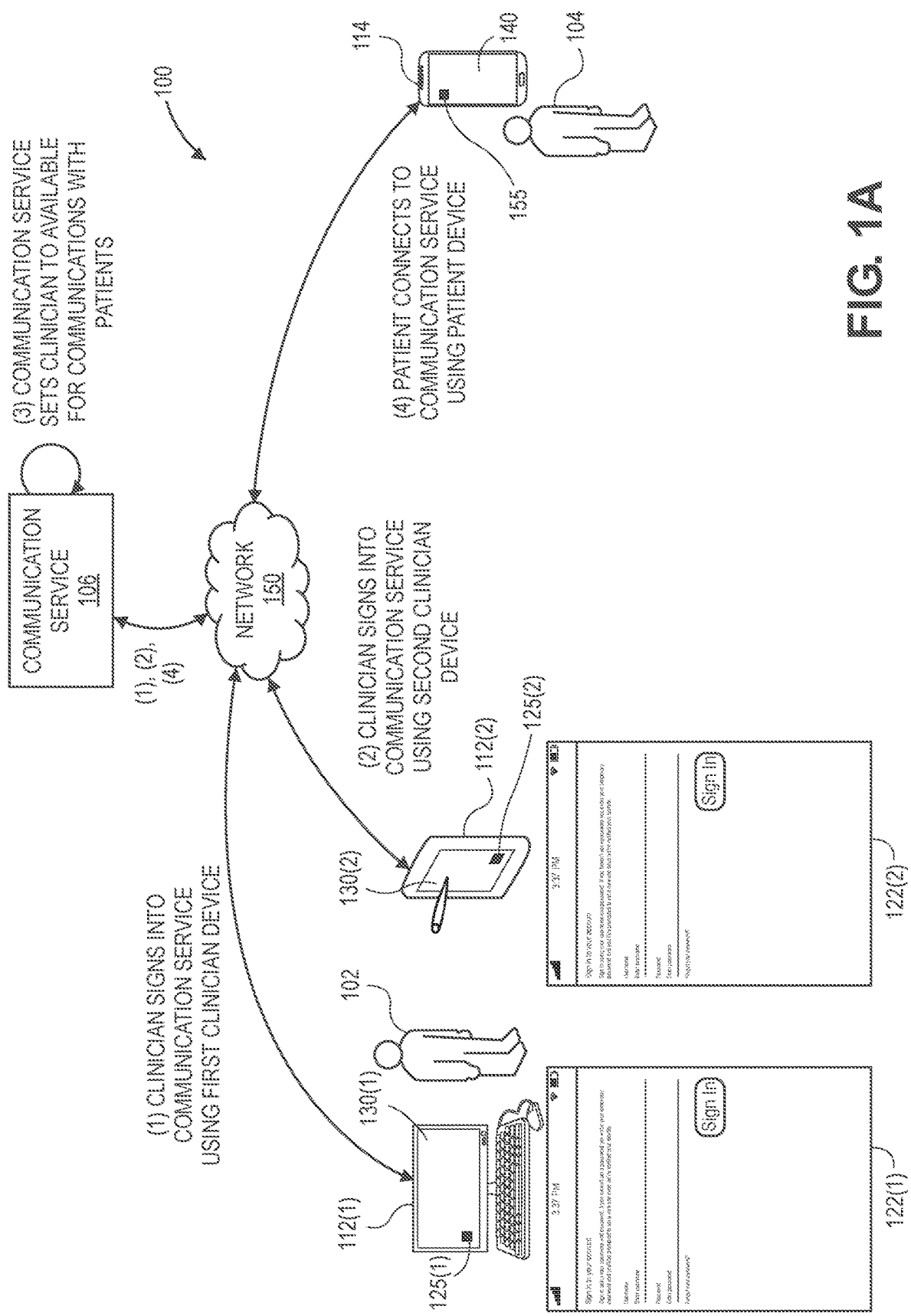
FIGS. 1A through 1B is an example transition diagram of establishing a multi-channel communication session between a patient device, a first clinician device, and a second clinician device, in accordance with implementations of the present disclosure.

As set forth in greater detail below, the disclose implementations provide a system and method for real-time or near real-time multi-channel communication between two or more participants in which one of those participants utilizes two devices to communicate with a single device of the other participant.

The disclosed implementations have particular applicability in network (aka online) based healthcare environments in which patients utilize a patient device, such as a laptop, cellphone, computer, etc., to participate in a communication session with a clinician (e.g., doctor, nurse, therapist, etc.). For example, a communication session may be established between a clinician and a patient by establishing a first connection between a first clinician device, such as a laptop, computer, etc., and a patient device and establishing a second connection between a second clinician device, such as a tablet, and the patient device. Audio and/or video ("A/V") data may be bi-directionally exchanged between the first clinician device and the patient device so that the patient and clinician can visually see and hear one another during the communication session. In addition, the clinician may access, using the second clinician device, one or more templates that are presented on the second clinician device display, annotate the presented template, and an annotated image that includes the annotation and the template may be sent via the second connection from the second clinician device to the patient device for presentation on the patient device display so that the patient can visually see the annotations made by the clinician to the presented template. For example, if the patient is experiencing stomach or intestinal pain, the clinician may select a template of the intestines of the human body, annotate that template with one or more words, arrows, drawings, etc., to convey a message intended by the clinician, and an annotated image of the template and the annotations may be sent from the second clinician device for presentation on the patient device display for viewing by the patient. As discussed further below, the annotated image is only sent to the patient device, is not sent to the first clinician device, and the A/V data of the patient presented by the first clinician device remains uninterrupted.

Through concurrent use of two clinician devices, as discussed herein, a clinician can simultaneously view and communicate with a patient while at the same time annotating and sharing other material such as templates with the patient as part of the communication session.

In addition to annotating templates, in some implementations, the patient may utilize the patient device to generate a patient image, such as a photograph of an area of concern on the patient's body, and the patient image will be sent to the second clinician device for presentation to the clinician via the second clinician device display, without disrupting the A/V data of the patient presented by the first clinician device. Similar to templates, the clinician may view the patient image on the second clinician device display and annotate the image. The second clinician device may then generate an annotated image that includes the annotations and the patient image and send the annotated image to the patient device for presentation to the patient, during the communication session and without disrupting the A/V data presented by the first clinician device and/or without sending the annotated image to the first clinician device.

In still further implementations, upon completion of the communication session, some or all annotated images may be associated with a patient record of the patient and maintained in a data store for later retrieval and/or viewing by the clinician and/or the patient.

Figure 1B:
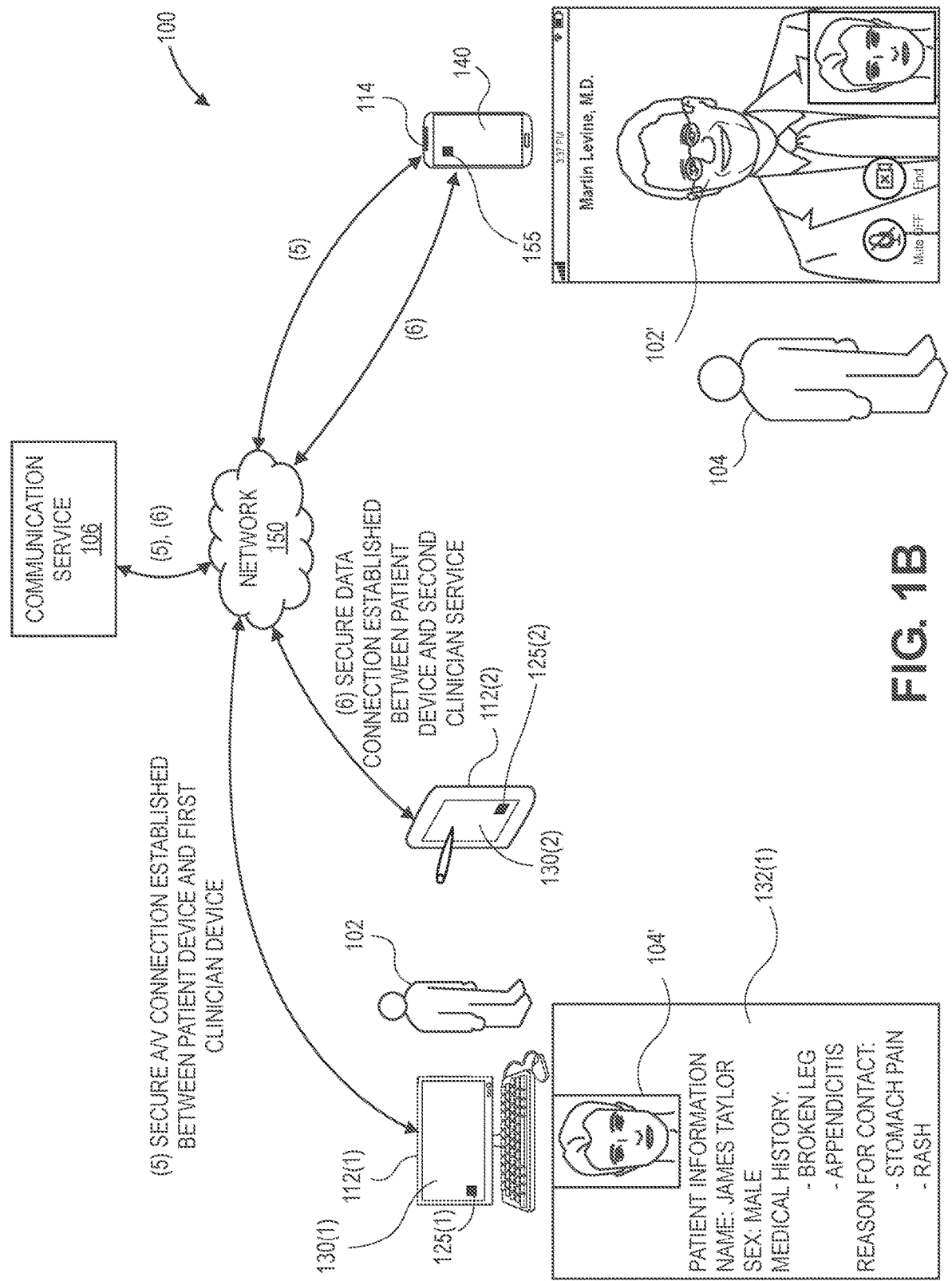

FIGS. 1A through 1B is an example transition diagram of establishing a multi-channel communication session between a patient device, a first clinician device and a second clinician device, in accordance with implementations of the present disclosure.

As illustrated, the environment 100 includes a communication service 106, which executes on one or more remote computing resources, a first clinician device 112(1) and first clinician device application 125(1), and a second clinician device 112(2) and second clinician device application 125(2) used by a clinician 102, and a patient device 114 and patient device application 155 used by a patient 104. Each of the communication service 106, first clinician device 112(1) and first clinician device application 125(1), second clinician device 112(2) and second clinician device application 125(2), and the patient device 114 and patient device application 155, may communicate through wired and/or wireless connections to a network 150, such as the Internet.

In some implementations, establishment of a communication session that includes the first clinician device application 125(1) executing on the first clinician device 112(1), second clinician device application 125(2) executing on the second clinician device 112(2), and the patient device application 155 executing on the patient device 114, may be facilitated or controlled by the communication service 106. For example, as discussed further below, the communication service may use a communications protocol, such as Web-Socket or WebRTC, to establish connections between the communication service and one or more of the first clinician device, the second clinician device, and/or the patient device. Those connections may then be used to establish a multi-channel communication session as discussed herein.

Referring first to FIG. 1A, in some implementations, a clinician 102, through interaction with the first clinician device application 125(1) may access or log into the communication service 106 through the first clinician device by submitting one or more credentials (e.g., username/password, biometrics, etc.) through a Sign-in interface 122(1) of the first clinician device application 125(1). Likewise, the same clinician 102 may also use the same credentials to access or log into the communication service 106 through the second clinician device by providing the credentials through a Sign-in interface 122(2) of the second clinician device application 125(2). By using the same credentials for both devices/clinician device applications, the communication service knows that both the first clinician device and the second clinician device are being used or available for use by the clinician 102 as part of a multi-channel communication session with a patient 104.

Upon receiving the credentials from the first clinician device 112(1) and the second clinician device 112(2), the communication service verifies the clinician 102 and indicates the clinician as available for communication sessions with patients.

Referring now to FIG. 1B, subsequent to the communication service indicating the clinician as available, in this example, a patient 104 connects to the communication service using a patient device application 155 executing on the patient device 114. Upon determining the patient and that the patient is to be connected to the clinician, a A/V connection is established between the first clinician device 112(1) and the patient device 114, and a data connection is established between the second clinician device 112(2) and the patient device 114. Through the A/V connection, the patient 104 is able to view on a patient device display a live video stream 102' of the clinician 102 and the clinician 102 is able to view on the first clinician device display 140 of the first clinician device 112(1) a live a video stream 104' of the patient 104. Noticeably, the video stream 102' of the clinician and the video stream 104' of the patient are not sent to the second clinician device. In addition, patient record information 132(1) corresponding to the patient 104 may also be obtained by the communication service 106 and sent to the first clinician device 112(1) for presentation on the first clinician device display 130(1) by the first clinician device application 125(1), as illustrated.

Through the A/V connection, the patient 104 and the clinician 102 may visually see each other and communicate through the A/V connection as if the patient and the clinician were together. At some point during the communication session, the clinician may wish to share other content with the patient and/or the patient may wish to share other content with the clinician.

Figure 2:
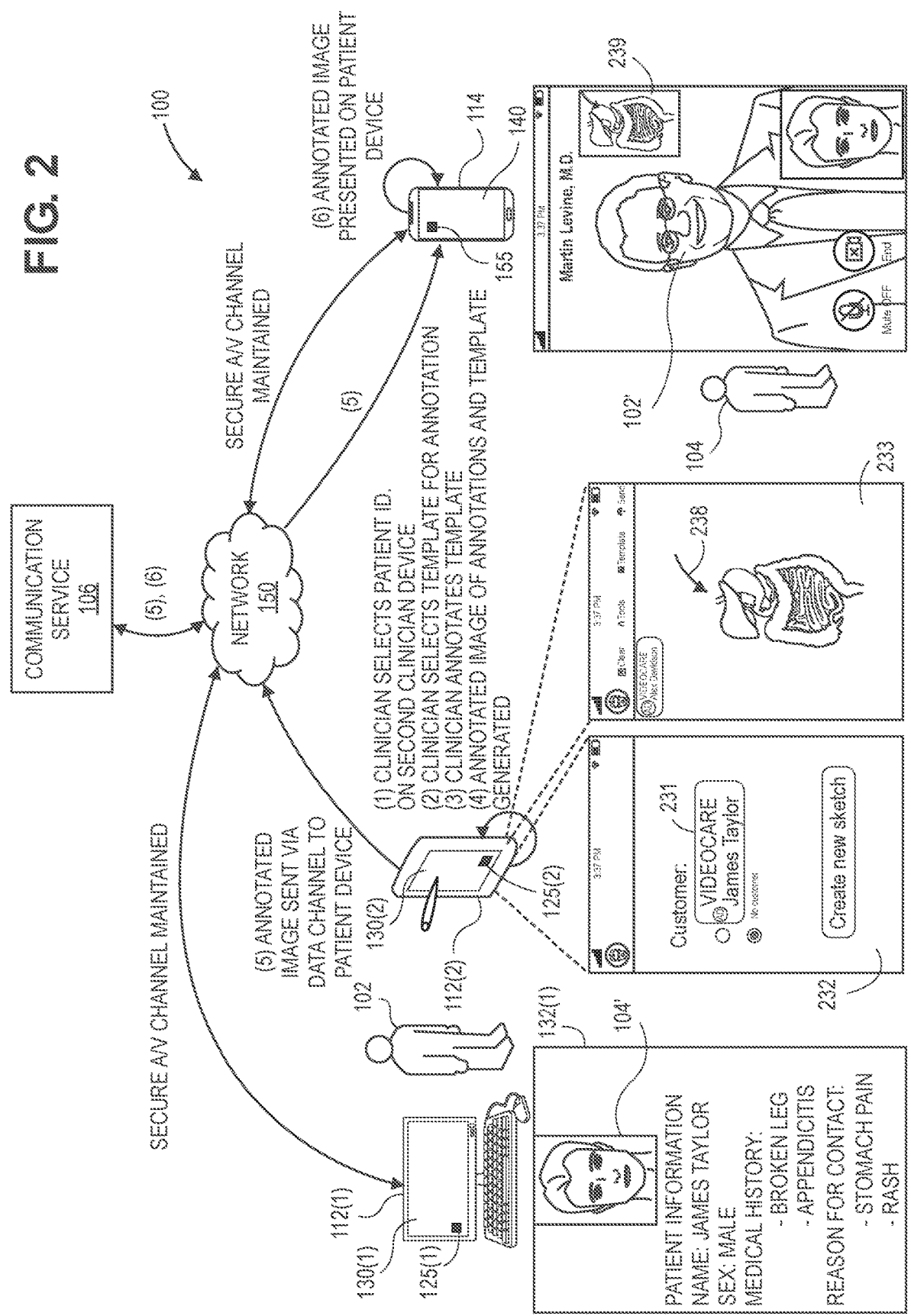
FIG. 2 is an example transition diagram of a clinician selecting a template at a second clinician device, annotating that template at the second clinician device, and an annotated image of the annotation and the template being sent from the second clinician device to the patient device as part of a communication session between the patient device, the first clinician device and the second clinician device, in accordance with disclosed implementations of the present disclosure.

For example, referring first to FIG. 2, a clinician may use the second clinician device 112(2) and second clinician device application 1340(2) executing thereon to share additional information with the patient, without disrupting the A/V connection between the first clinician device and the patient device. For example, the clinician 102 may select or pick up the second clinician device 112(2) and, through interaction with an acknowledgement interface 232 of the second clinician device application 130(2), verify that the clinician desires to utilize the second clinician device to exchange additional materials with the patient 104, in this example James Taylor, through selection of the control 231 that identifies the patient 104. Use of the acknowledgement interface 232 ensures that the clinician is sharing information with the correct patient and that the information is associated with the correct patient record.

Upon acknowledging the patient, the clinician 102, may select or be provided with one or more templates 233 that are presented by the second clinician device application 125(2) on the second clinician device display 130(2). In addition, the clinician 102 may provide annotations 238 to the template through interaction with the second clinician device display 130(2). For example, the second clinician device display 130(2) may be a touch-based display and the clinician 102 may annotate the template through interaction with the touch-based display of the second clinician device 112(2).

The second clinician device application 125(2) executing on the second clinician device 112(2) may determine when annotation of the template is complete and generate an annotated image, also referred to herein as image data, that includes the template 233 and the annotation 238. Annotation completion may be determined, for example by the clinician 102 indicating that annotation is complete (e.g., through selection of a complete control), based on a defined period of time elapsing without any further annotations to the template, etc.

The annotated image may then be sent from the second clinician device 112(2) for display as annotated image 239 on the patient device display 155 of the patient device 114 so that the patient 104 can visually see the template 233 and the annotation 238 as generated by the clinician 102, concurrent with the A/V connection with the clinician 102'. As illustrated, the annotated image is sent through the data connection between the second clinician device 112(2) and the patient device 114 while the A/V connection between the first clinician device 112(1) and the patient device 114 is maintained and without interfering with the A/V connection. In particular, the annotated image is not sent to the first clinician device 112(1) or presented on the first clinician device display 130(1) even though the first clinician device 112(1) is also included in the communication session.

Figure 3A:
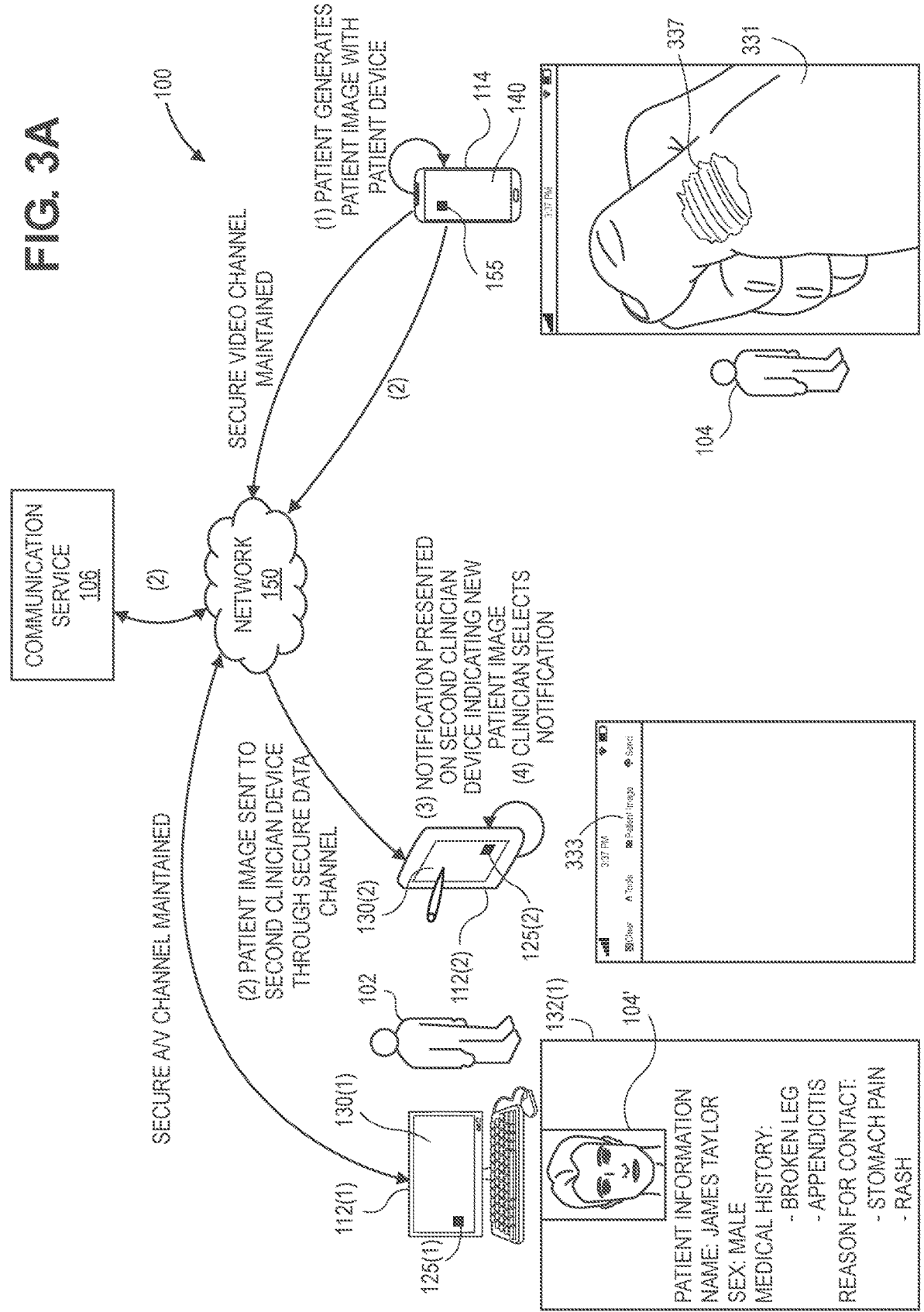
FIG. 3A is an example transition diagram of a patient generating a patient image with a patient device and transmission of that patient image from the patient device to the second clinician device as part of a communication session between the patient device, the first clinician device and the second clinician device, in accordance with the disclosed implementations of the present disclosure.
Figure 3B:
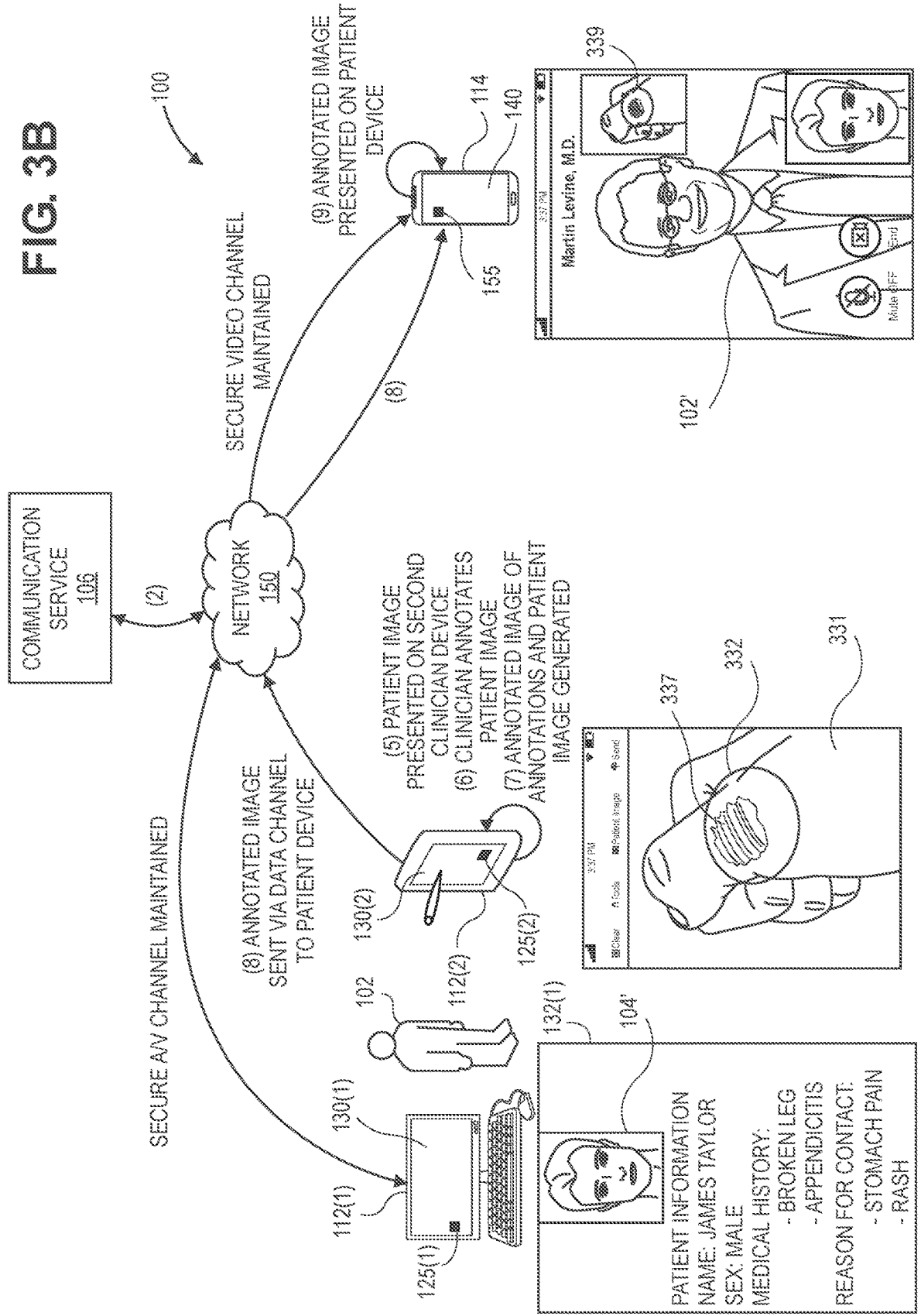
FIG. 3B is an example transition diagram of a clinician annotating, on the second clinician device, the patient image, and an annotated image of the annotation and the patient image being sent from the second clinician device to the patient device as part of a communication session between the patient device, the first clinician device and the second clinician device, in accordance with disclosed implementations of the present disclosure.

In other implementations, the patient may send patient images for review and/or annotation by the clinician. For example, referring to FIGS. 3A through 3B illustrated is an example transition diagram of a patient generating a patient image 331 with a patient device 114, transmission of that patient image 331 from the patient device to the second clinician device, and annotation of the patient image by the clinician, in accordance with disclosed implementations of the present disclosure. As will be appreciated, like the example discussed with respect to FIG. 2, the example illustrated in FIGS. 3A through 3B is performed during a multi-channel communication session established and maintained as discussed above with respect to FIGS. 1A through 1B.

Turning first to FIG. 3A, a patient 104 using an imaging element (e.g., camera) of the patient device 114, or through selecting of an existing image stored on the patient device, generates a patient image 331 that the patient desires to share with the clinician 102. In this example, the patient 104 uses a camera of the patient device 114 to generate a patient image of a rash 337 on the patient's hand. For example, using a patient device application 155 on the patient device 114, the patient may select an image control that actives a rear facing camera on the patient device 114 to allow the patient 104 to generate the patient image 331. Alternatively, the patient 104 may select an existing image stored in a memory of the patient device 114 as the patient image 331.

Upon generation or selection of a patient image 331, the patient image 331 is transmitted via the data connection between the patient device 114 to the second clinician device 112(2). For example, the patient image 331 may be sent from the patient device 114 to the communication service 106 and the communication service, having knowledge that the clinician 102 has signed into the communication service using both the first clinician device and the second clinician device, as discussed above, may cause a notification 333 to be presented on the second clinician device display 130(2) by the second clinician device application 125(2) indicating that a patient image has been received. The clinician 102 may select the notification to view the patient image.

As illustrated, even though the first clinician device 112(1) and the second clinician device 112(2) are included in the communication session, the patient image 331 is not sent to the first clinician device 112(1) and the A/V connection between the first clinician device 112(1) and the patient device 114 remains uninterrupted. As a result, the patient and clinician are able to continue their A/V-based communication and concurrently share other information, such as the patient image, templates, annotations, etc., via the patient device 114 and the second clinician device 112(2) without disrupting that A/V communication.

Referring now to FIG. 3B, upon selection of the notification 333 by the clinician 102, the patient image 331 is presented on the second clinician device display 130(2) of the second clinician device 112(2). Similar to annotating the template, as discussed above, the clinician, while communicating with the patient, may annotate 332 the patient image 331 presented on the second clinician device display. A determination is then made that the annotation is complete and an annotated image 339 that includes both the annotation and the patient image is generated by the second clinician device application 125(2) executing on the second clinician device 112(2). The annotated image is then sent from the second clinician device 112(2) for presentation on the patient device display 140 of the patient device as annotated image 339.

Similar to the exchange of the patient image 331 and the annotated image 239 of the template and annotations of the template, the annotated image 339 of the annotations and the patient image is sent between the second clinician device 112(2) and the patient device 114 without sending the annotated image to the first clinician device 112(1), even though the first clinician device 112(1) is included in the communication session.

As illustrated in the examples discussed with respect to FIGS. 1A through 3B, a multi-channel communication session may be established between a first clinician device 112(1), a second clinician device 112(2), and a patient device 114 that enables bi-directional A/V communication and concurrent exchange of other data such as images and annotations without disrupting or interfering with the A/V communication. Such implementations provide an improvement of existing techniques for network-based communication by enabling selective delivery of content (e.g., A/V and data) to different devices included in the communication session. In the illustrated examples, the clinician is using a first clinician device to visually communicate with the patient and simultaneously using a second clinician device to share other information with the patient, in this example, annotations of templates and/or patient images provided by the patient.

As will be appreciated, during a communication session, there may be multiple exchanges of templates, patient images, annotated images, and/or other information between the patient device and the second clinician device. For example, a clinician may annotate a template and a first annotated image of the annotation and the template may be sent to the patient device, a patient may then generate and send a patient image that is then annotated by the clinician at the second clinician device and a second annotated image of the annotation and the patient image generated and sent back to the patient device. Any number of exchanges of annotated images, patient images, and/or other information may occur during a single communication session without disrupting or interfering with the A/V communication between the clinician and the patient.

Likewise, while the examples discussed herein focus primarily on a communication session between a clinician and a patient, the disclosed implementations are equally applicable to any communication session between any two or more participants. For example, the implementations may be used to establish and maintain a multi-channel communication session between a teacher using a first teacher device and a second teacher device and a student using a student device. Likewise, some implementations may include more than two individuals in a communication session in which one or more of the individuals use one device for A/V communication and a separate device for data exchange. Accordingly, the disclosed implements should not be limited to the examples of the patient/clinician discussed herein.

Figure 4:
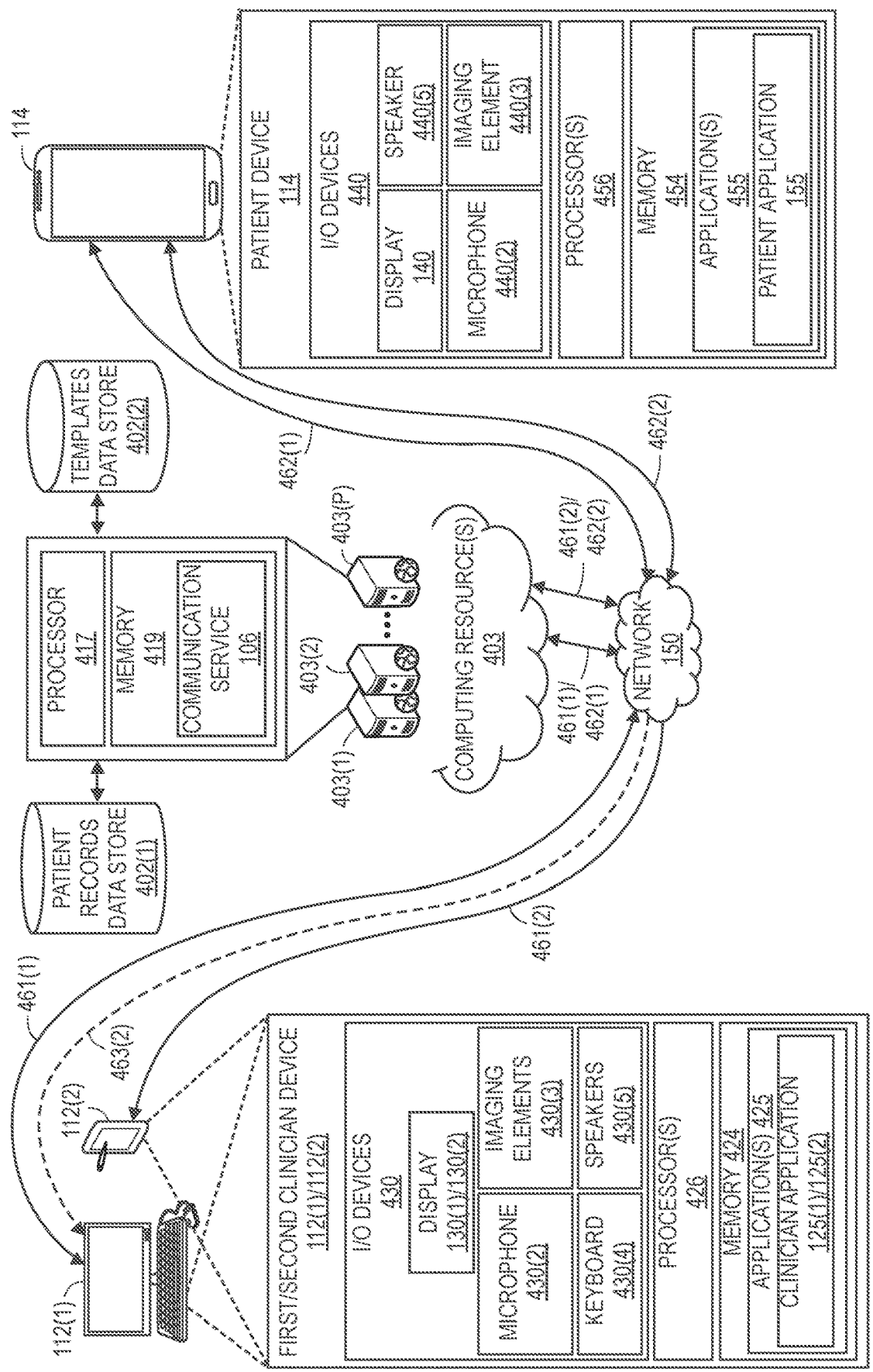
FIG. 4 is a block diagram of an example system that includes a communication service, a first clinician device, a second clinician device, a patient device, and communication connections therebetween, in accordance with disclosed implementations of the present disclosure.

FIG. 4 is a block diagram of an example system that includes a communication service, a first clinician device, a second clinician device, a patient device, and communication connections therebetween, in accordance with disclosed implementations of the present disclosure.

As illustrated, the patient device 114 may be any portable device such as a tablet, cellular phone, laptop, wearable, etc. The patient device 114 may include one or more input/output devices 140, including, but not limited to a display 140(1), microphone 140(2), imaging element 140(3), speakers 140(5), etc. The display 140(1) may be any type of display, such as a touch-based display, etc. The imaging element 140(3) of the patient device 114 may comprise any form of optical recording sensor 422 or device that may be used to photograph or otherwise record information or data.

As shown in FIG. 4, the patient device 114 is connected to the network 150 and includes one or more memory 454 or storage components (e.g., a database or another data store), one or more processors 456, I/O devices 140, and any other components that may be required in order to capture, receive, store and/or transmit data, such as video, patient images, annotated images, etc. For example, the imaging element 140(3) may capture one or more still or moving images. The patient device 114 may also connect to or otherwise communicate with the network 150 through the sending and receiving of digital data.

The patient device 114 may also include one or more applications 155, such as patient device application 155(1), stored in memory that may be executed by the one or more processors 456 of the patient device to cause the processor of the patient device to perform various functions or actions. For example, when executed, the patient device application 155(1) may verify the identity of the user, request or receive from the patient a session purpose for a communication session, connect to the communication service 106, access and/or provide patient records to the patient, etc. As another example, the patient device application 155(1) may access the imaging element 140(3) of the patient device 114 and generate a patient image that is sent to the communication service 106 and/or the second clinician device 112(2). In still other examples, the patient device application 155(1) may provide an interface to enable viewing of video of a clinician sent from the first clinician device 112(1) and/or annotated images sent from the second clinician device 112(2), thereby providing the patient with an application that facilities a multi-channel communication with a clinician.

The first clinician device 112(1) and the second clinician device 112(2) may be any type of device such as a laptop, desktop, dedicated computing device, tablet, etc. In the examples discussed above, and as illustrated in FIG. 4, the first clinician device 112(1) is a desktop or laptop computing device and the second clinician device 112(2) is a tablet device. As is known, such devices may include similar components. As such, the components are discussed herein together. However, it will be understood that the first clinician device 112(1) and the second clinician device 112(2) are independent and separate devices and each includes its own respective components, applications, etc.

The first clinician device 112(1) and the second clinician device 112(2) may each include one or more input/output devices 430, including, but not limited to a display 130(1)/130(2), microphone 430(2), imaging element 430(3), keyboard 430(4), and/or speakers 430(5). The display 430(1) may be any type of display, such as a touch-based display, etc. The imaging element 430(3) may comprise any form of optical recording sensor 422 or device that may be used to photograph or otherwise record information or data. In some implementations, the second clinician device 112(2) may or may not include a keyboard and/or the keyboard may be presented on the display of the second clinician device when needed for input.

As is shown in FIG. 4, the first clinician device 112(1) and the second clinician device 112(2) are each connected to the network 150 and each include one or more memory 424 or storage components (e.g., a database or another data store), one or more processors 426, I/O devices 430, and any other components that may be required in order to capture, receive, store and/or transmit data, such as video, templates, annotated images, etc. For example, the imaging element 430(3) of the first clinician device 112(1) may capture one or more still or moving images. The first clinician device 112(1) and the second clinician device 112(2) may also connect to or otherwise communicate with the network 150 through the sending and receiving of digital data.

The first clinician device 112(1) and second clinician device 112(2) may each also include one or more applications 125, such as clinician device application 125(1)/125(2), stored in memory that may be executed by the one or more processors 426 of the first clinician device/second clinician device to cause the processor of the first clinician device/second clinician device to perform various functions or actions. For example, when executed on the first clinician device 112(1), the first clinician device application 125(1) may verify the identity of the clinician, connect to the communication service 106, receive and present patient records relating to a patient involved in a communication session, etc. As another example, the second clinician device application 125(2) executing on the second clinician device 112(2) may verify the identity of the clinician, connect to the communication service 106, receive and present templates for annotation by the clinician during a communication session, generate annotated images that include annotations and a template or patient image that has been annotated, etc.

The patient device application 155(1) and/or the clinician device applications 125(1) executing on the first clinician device 112(1) and/or the second clinician device 112(2) may communicate, via network 150 with the communication service 106 and/or with each other. Generally, the communication service 106 includes or executes on computing resource(s) 403. The computing resource(s) 403 are separate from the patient device 114, separate from the first clinician device 112(1) and separate from the second clinician device 112(2). Likewise, the computing resource(s) 403 may be configured to communicate over the network 150 with the patient device 114, the first clinician device 112(1), the second clinician device 112(2), and/or other external computing resources, data stores, such as patient records data store 402(1) and/or templates data store 402(2), etc.

As illustrated, the computing resource(s) 403 may be remote from the patient device 114, first clinician device 112(1), and the second clinician device 112(2), and implemented as one or more servers 403(1), 403(2), . . . , 403(P) and may, in some instances, form a portion of a network-accessible computing platform implemented as a computing infrastructure of processors, storage, software, data access, and so forth that is maintained and accessible by components/devices of the communication service 106, the patient device 114, the first clinician device 112(1), and the second clinician device 112(2), via the network 150, such as an intranet (e.g., local area network), the Internet, etc.

The computing resource(s) 403 do not require end-user knowledge of the physical location and configuration of the system that delivers the services. Common expressions associated for these remote computing resource(s) 403 include "on-demand computing," "software as a service (SaaS)," "platform computing," "network-accessible platform," "cloud services," "data centers," and so forth. Each of the servers 403(1) through (P) include a processor 417 and memory 419, which may store or otherwise have access to the communication service 106.

The network 150 may be any wired network, wireless network, or combination thereof, and may comprise the Internet in whole or in part. In addition, the network 150 may be a personal area network, local area network, wide area network, cable network, satellite network, cellular telephone network, or combination thereof. The network 150 may also be a publicly accessible network of linked networks, possibly operated by various distinct parties, such as the Internet. In some implementations, the network 150 may be a private or semi-private network, such as a corporate or university intranet. The network 150 may include one or more wireless networks, such as a Global System for Mobile Communications (GSM) network, a Code Division Multiple Access (CDMA) network, a Long Term Evolution (LTE) network, or some other type of wireless network. A variety of protocols and components for communicating via the Internet or any of the other aforementioned types of communication networks may be used with the disclosed implementations. For example, WebSocket and/or WebRTC may be used to established connections between the devices 112(1), 112(2), 114, and/or the computing resources 403. In one implementation, WebRTC and/or the WebSocket protocol may be used to establish a A/V connection 461(1)/462(1) between the first clinician device 112(1) and the patient device 114. Likewise, in some implementations, the signaling channel used to establish the A/V connection 461(1)/462(1) between the first clinician device 112(1) and the client device 114 may also be used as the data connection 461(2)/462(2) between the second clinician device 112(2) and the patient device 114.

In other implementations other communication protocols may be used to establish and maintain the A/V connection 462(1) and/or the data connection 462(2) between the computing resources 403 and the patient device 114, the A/V connection 461(1) between the first clinician device 112(1) and the computing resources 403, and/or the data connection 461(2) between the second clinician device 112(2) and the computing resources 403 may be utilized. In some implementations, a data connection 463(2) may also be established between the first clinician device 112(1) and the computing resources 403. For example, the data connection 463(2) may be used to send data, such as a session completion interface, patient records, etc., to the first clinician device 112(1) as part of the communication session.

The computing resources may also include or connect to one or more data stores, such as the patient records data store 402(1) and/or the templates data store 402(2). The patient records data store 402(1) may include patient records, annotated images, clinician notes relating to a patient, etc. Any of a variety of storage techniques may be utilized to secure storage of the patient records in compliance with any and all privacy and security measures.

The templates data store includes templates that may be selected or provided to the second clinician device 112(2) for annotation by a clinician during a communication session between a clinician and a patient. As discussed herein, the templates may be searched for and selected by the clinician and/or the communication service may determine templates to suggest or recommend to the clinician based on a provided and/or determined session purpose of the communication session.

The computers, servers, data stores, devices and the like described herein have the necessary electronics, software, memory, storage, databases, firmware, logic/state machines, microprocessors, communication links, displays or other visual or audio user interfaces, printing devices, and any other input/output interfaces to provide any of the functions or services described herein and/or achieve the results described herein. Also, those of ordinary skill in the pertinent art will recognize that users of such computers, servers, devices and the like may operate a keyboard, keypad, mouse, stylus, touch screen, or other device (not shown) or method to interact with the computers, servers, devices and the like, or to "select" or generate an item, template, annotated image, patient image, and/or any other aspect of the present disclosure.

The communication service 106, the device applications 125/155, the patient device 114, the first clinician device 112(1), and/or the second clinician device 112(2) may use any web-enabled or Internet applications or features, or any other client-server applications or features including E-mail or other messaging techniques, to connect to the network 150, or to communicate with one another, such as through short or multimedia messaging service (SMS or MMS) text messages. For example, the servers 403(1), 403(2) . . . 403(P) may be adapted to transmit information or data in the form of synchronous or asynchronous messages from the communication service 106 to the processor 426/456 or other components of the patient device 114, first clinician device 112(1), second clinician device 112(2), or any other computer device in real time or in near-real time, or in one or more offline processes, via the network 150.

The data and/or computer executable instructions, programs, firmware, software and the like (also referred to herein as "computer executable" components) described herein may be stored on a computer-readable medium that is within or accessible by computers or computer components such as the servers 403(1), 403(2) . . . 403(P), the processor 426/456, or any other computers or control systems utilized by the device application 125/155, the communication service 106, the patient device 114, the first clinician device 112(1), and/or the second clinician device 112(2), and having sequences of instructions which, when executed by a processor (e.g., a central processing unit, or "CPU"), cause the processor to perform all or a portion of the functions, services and/or methods described herein. Such computer executable instructions, programs, software and the like may be loaded into the memory of one or more computers using a drive mechanism associated with the computer readable medium, such as a floppy drive, CD-ROM drive, DVD-ROM drive, network interface, or the like, or via external connections.

Some implementations of the systems and methods of the present disclosure may also be provided as a computer-executable program product including a non-transitory machine-readable storage medium having stored thereon instructions (in compressed or uncompressed form) that may be used to program a computer (or other electronic device) to perform processes or methods described herein. The machine-readable storage media of the present disclosure may include, but is not limited to, hard drives, floppy diskettes, optical disks, CD-ROMs, DVDs, ROMs, RAMs, erasable programmable ROMs ("EPROM"), electrically erasable programmable ROMs ("EEPROM"), flash memory, magnetic or optical cards, solid-state memory devices, or other types of media/machine-readable medium that may be suitable for storing electronic instructions. Further, implementations may also be provided as a computer executable program product that includes a transitory machine-readable signal (in compressed or uncompressed form). Examples of machine-readable signals, whether modulated using a carrier or not, may include, but are not limited to, signals that a computer system or machine hosting or running a computer program can be configured to access, or including signals that may be downloaded through the Internet or other networks.

Figure 5:
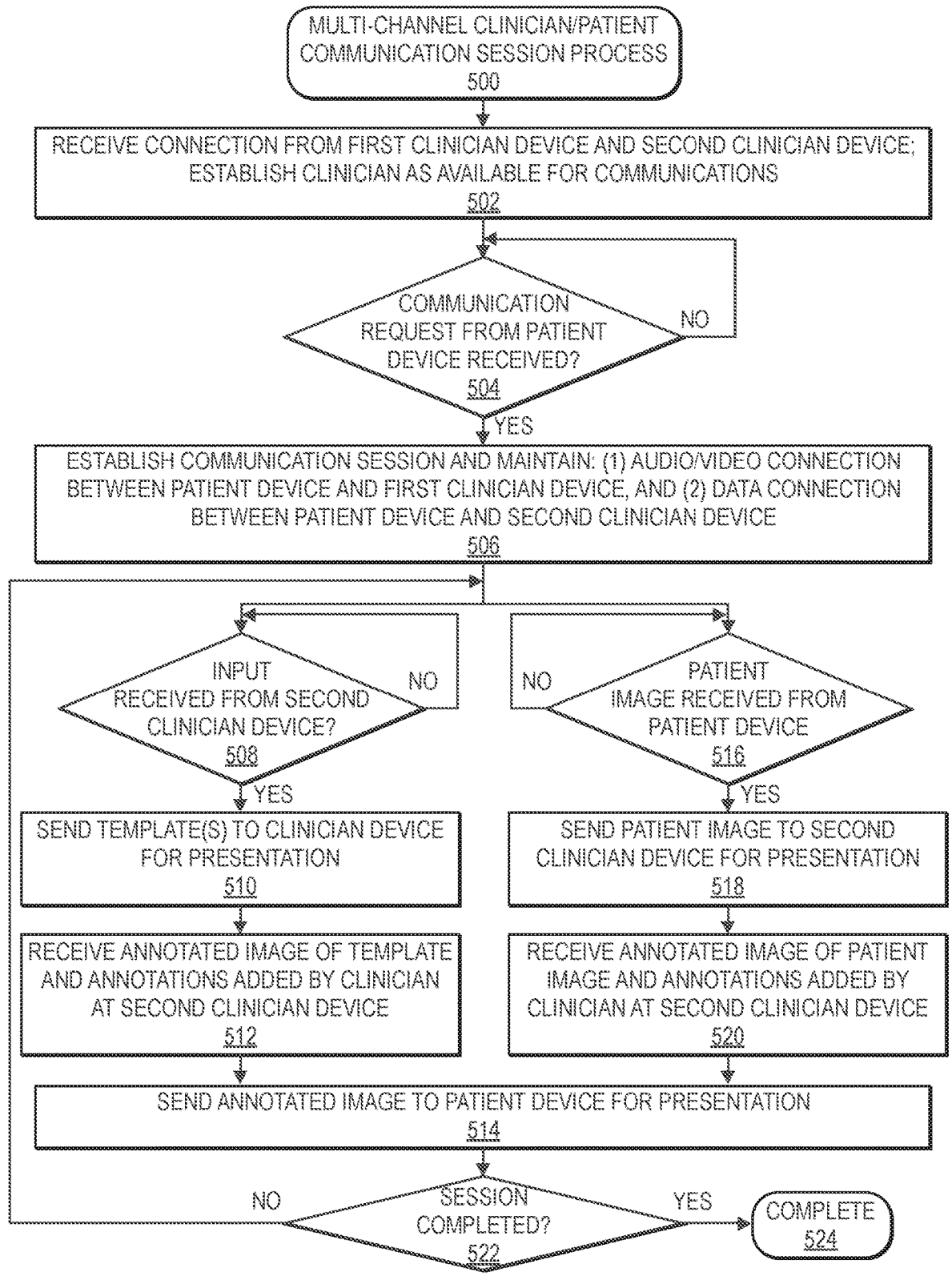
FIG. 5 is an example multi-channel clinician/patient communication session process, in accordance with disclosed implementations of the present disclosure.

FIG. 5 is an example multi-channel clinician/patient communication session process 500, in accordance with disclosed implementations of the present disclosure. The example process 500 begins upon receipt of a connection from a first clinician device and a second clinician device, as in 502. For example, as discussed above, a clinician may sign into or connect to the communication service through clinician device applications executing on the first clinician device and the second clinician device. Once the clinician is connected, the clinician may be indicated as available to participate in a communication session with a patient, as in 502.

The example process also determines if a communication request has been received from a patient, as in 504. For example, a patient, accessing the communication service through a patient device application executing on a patient device, may request to initiate a communication session with a clinician. If it is determined that a communication request has not been received, the example process 500 returns to block 504 and continues.

If it is determined that a communication request has been received, a communication session is established and maintained that includes an A/V connection between the patient device and the first clinician device and a data connection between the patient device and the second clinician device, as in 506. For example, the A/V connection and/or data connection may be established using a WebSocket and/or WebRTC between the patient device, communication service, first clinician device, and second clinician device. In other implementations, other communication techniques may be utilized.

Upon establishment of the communication session, a determination is made as to whether an input is received from the second clinician device, as in 508. An input may include, for example, the clinician selecting or activating the second clinician device with the intent to share materials (e.g., templates, annotations, annotated images) with the patient. If it is determined that an input has not been received, the example process returns to block 508 and continues. If it is determined that an input has been received, one or more templates are selected and sent to the second clinician device for presentation on the second clinician device display, as in 510. As discussed further below, templates may be selected, for example, in response to a search or input term submitted by the clinician, a session intent of the communication session as provided by the clinician, patient, or determined from the communication session, based on the patient record of the patient, etc.

Subsequent to sending the template for presentation on the second clinician device display, an annotated image that includes the template and annotations input by the clinician at the second clinician device are received from the second clinician device, as in 512. As discussed above, the second clinician device application executing on the second clinician device may present the template and the clinician may annotate the template by providing input (e.g., touch-based display inputs) at the second clinician device. Upon determination that the annotations have completed, the second clinician device application executing on the second clinician device may generate and send an annotated image that includes the template and the annotations.

Completion of the annotation may be determined, for example, in response to the clinician indicating that the annotation has completed, upon expiration of a defined period of time with no additional annotations provided, etc.

The received annotated image is then sent to the patient device for presentation on the patient device display, as in 514. As discussed above, the patient may concurrently view annotated images that include templates or other material annotated by the clinician on the second clinician device and view/correspond with the clinician. In addition, the annotated image is sent to the patient device without sending the annotated image to the first clinician device, thereby enabling the clinician to continue to view the A/V communication from the patient device and/or patient records of the patient.

Concurrent with blocks 508 through 512, the example process 500 may also determine if a patient image has been received from a patient device, as in 516. For example, as discussed above, a patient may use an imaging element of the patient device to generate an image that is sent by the patient device application executing on the patient device to the communication service. If it is determined that a patient image has not been provided, the example process 500 returns to block 516 and continues.

If it is determined that a patient image has been received from the patient device, the patient image is sent to the second clinician device for presentation, as in 518. As discussed, the patient image is sent without interfering or interrupting the A/V communication between the patient device and the first clinician device. Likewise, the patient image is not sent to the first clinician device.

Subsequent to sending the patient image for presentation on the second clinician device display, an annotated image that includes the patient image and annotations input by the clinician at the second clinician device are received from the second clinician device, as in 520. As discussed above, the second clinician device application executing on the second clinician device may present the patient image and the clinician may annotate the patient image by providing input (e.g., touch-based display inputs) at the second clinician device. Upon determination that the annotations have completed, the second clinician device application executing on the second clinician device may generate and send an annotated image that includes the patient image and the annotations.

Completion of the annotation may be determined, for example, in response to the clinician indicating that the annotation has completed, upon expiration of a defined period of time with no additional annotations provided, etc.

The received annotated image is then sent to the patient device for presentation on the patient device display, as in 514. As discussed above, the patient may concurrently view annotated images that include templates/patient images or other material annotated by the clinician on the second clinician device and view/correspond with the clinician. In addition, the annotated image is sent to the patient device without sending the patient image to the first clinician device, thereby enabling the clinician to continue to view the A/V communication from the patient device and/or patient records of the patient.

Finally, a determination is made as to whether the communication session has completed, as in 522. If it is determined that the communication session has not completed, the example process 500 returns to decision blocks 508/516 and continues. If it is determined that the communication has completed, the example process 500 completes, as in 524.

The example discussed with respect to FIG. 5 may be performed by a communication service 106 that facilitates communication between the first clinician device/second clinician device and the patient device. In other implementations, the detection and exchange of information (e.g., annotated images, patient images, templates, etc.) may be exchanged directly between the first clinician device/second clinician device and the patent device. For example, the processes performed at blocks 508, 510, 512, 514 may be performed by a second clinician device application executing on the second clinician device and/or by the second clinician device application executing on the second clinician device in conjunction with the communication service. Likewise, the processes performed at blocks 516, 518, and 520 may be performed by and directly between the patient device and the second clinician device. For example, the patent device/patient device application may determine if an image has been received (decision block 516) and send the patient image to the second clinician device for presentation (block 518). The second clinician device/second clinician device application may receive an annotated image of the patient image as annotated by the clinician using the second clinician device (block 520).

Figure 6:
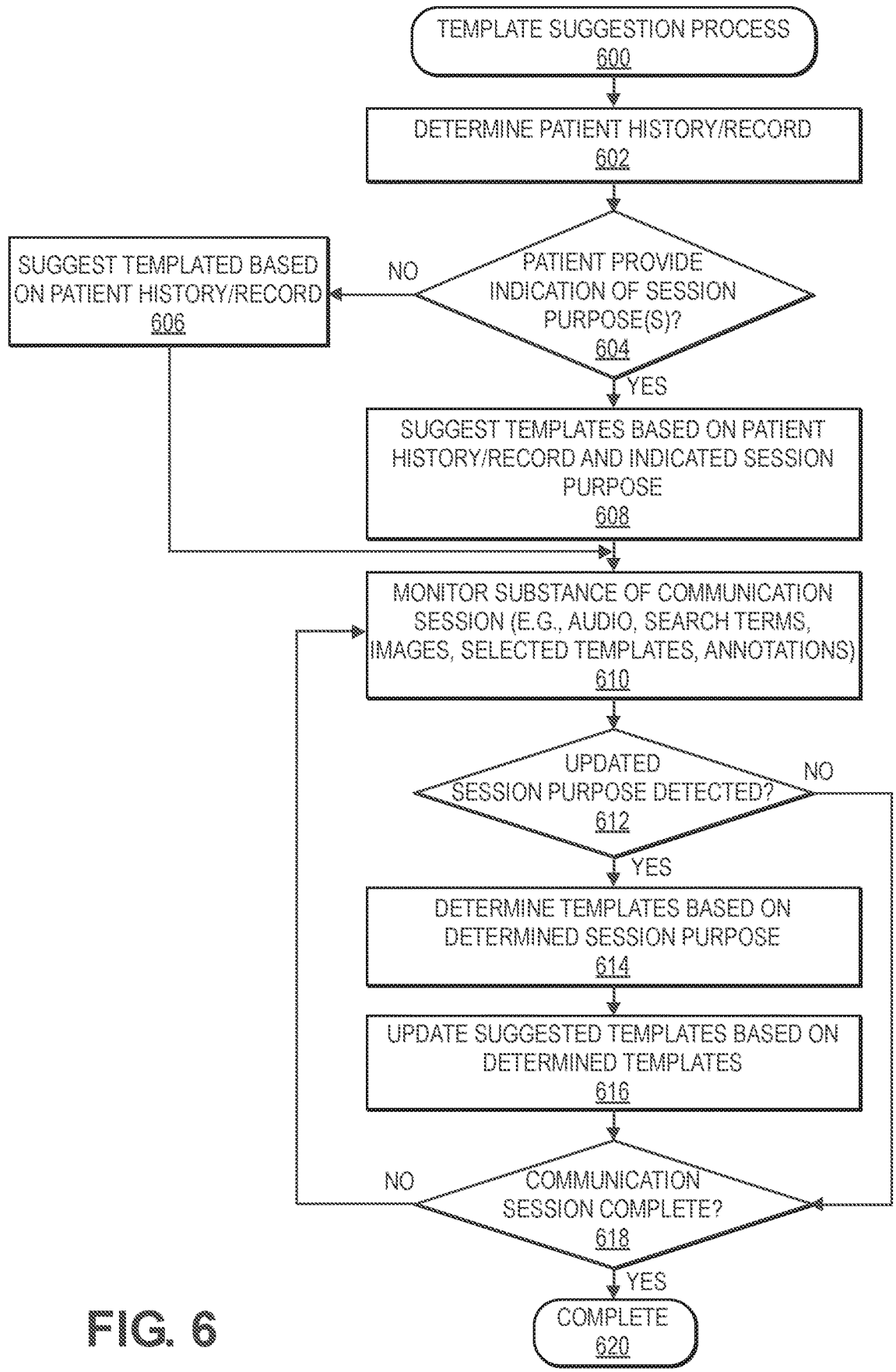
FIG. 6 is an example template suggestion process, in accordance with disclosed implementations of the present disclosure.

FIG. 6 is an example template suggestion process 600, in accordance with disclosed implementations of the present disclosure. As discussed above, templates may be determined and sent to the second clinician device for annotation by the clinician as part of a communication session with a patient. The example process 600 may be performed by the communication service alone, by the second clinician device application alone, or by both the communication service and the second clinician device application working together.

The example process 600 begins by determining the patient history or obtaining the patient record from the patient record data store for the patient initiating or involved in the communication session, as in 602.

A determination may also be made as to whether the patient provided an indication of a session purpose for the communication session, as in 604. For example, when requesting a communication session, the patient may be asked to indicate or provide a session purpose for the communication session. Alternatively, or in addition thereto, if the communication session is a scheduled communication session, the session intent may be indicated in or at the time of scheduling the communication session. If it is determined that the patient did not provide an indication of a session purpose, one or more templates may be determined and suggested based on the patient history/record of the patient, as in 606. For example, if the patient has had prior communications, etc., it may be determined that the patient is following-up on those prior communications and templates relating to the session purpose of those prior communications may be suggested.

In comparison, if the patient provided a session purpose or the session purpose is otherwise known/determined, one or more templates may be determined and suggested based on the patient history/record and based on the indicated session purpose, as in 608.

In addition to suggesting one or more templates at the initiation of the communication session, the example process may monitor for a substance of the communication session that may be used to determine an updated session purpose of the communication session or a change in the session purpose of the communication session, as in 610. For example, one or more automatic speech recognition engines ("ASR") and/or natural language processing ("NLP") engines may process a portion or all the speech included in the communication session to determine a substance of the communication session. Alternatively, or in addition thereto, patient images, templates selected by the clinician, and/or annotated images may be processed using one or more image processing algorithms to determine a substance of the communication session. As still another example, keywords or other inputs or indicators included in the communication session may be processed by the example process 600 to determine a substance of the communication session and the corresponding session purpose or updated session purpose of the communication session (generally referred to herein as the session purpose).

A determination is then made as to whether an updated session purpose has been determined, as in 612. If an updated session purpose is determined during the communication session, one or more templates are determined based on the updated session purpose, as in 614. The suggested templates may then be updated to include the templates determined from the updated session purpose, as in 616.

The suggested templates/updated suggested templates, may be sent to and/or presented on the second clinician device display for selection by the clinician as part of the communication service, as discussed herein.

Upon updating the suggested templates or if it is determined at decision block 612 that an updated session purpose has not been determined, a determination is made as to whether the communication session has completed, as in 618. If it is determined that the communication session has not completed, the example process 618 returns to block 610 and continues. If it is determined that the communication session has completed, the example process 600 completes, as in 620.

Figure 7:
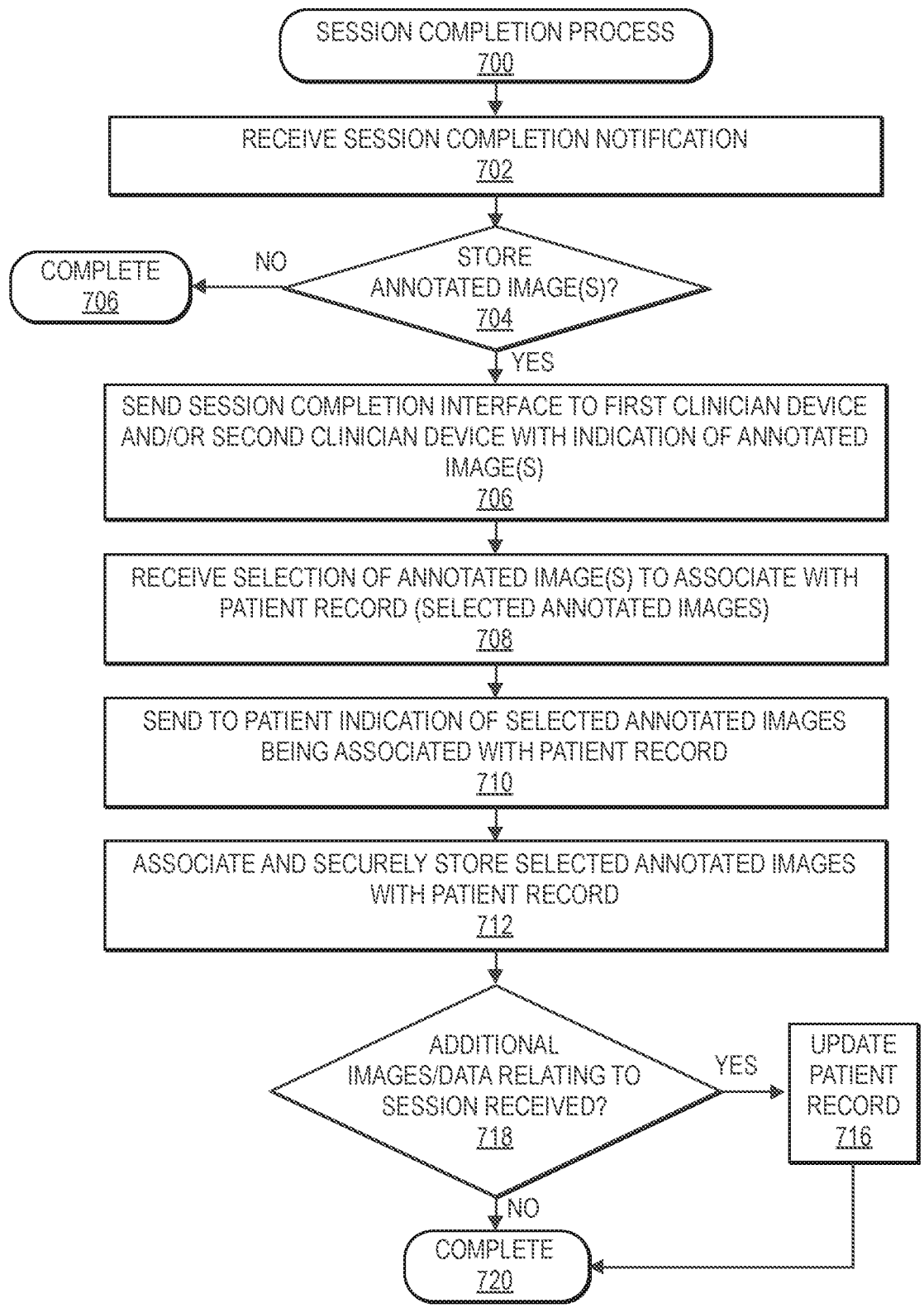
FIG. 7 is an example session completion process, in accordance with disclosed implementations of the present disclosure.

FIG. 7 is an example session completion process 700, in accordance with disclosed implementations of the present disclosure. The example process 700 may be performed by the communication service alone, by the first clinician device application alone, by the second clinician device application alone, or by some or all of the communication service, the first clinician device application, and/or the second clinician device application working together.

The example process 700 begins upon receipt of a session completion notification, as in 702. A session completion notification may be received when the communication session is terminated. If it is determined that the communication session has completed, a determination is made as to whether one or more annotated images from the communication session are to be stored and associated with the patient record of the patient included in the communication session, as in 704. If annotated images are not to be associated and stored, the example process completes, as in 706.

If it is determined that one or more annotated images are to be associated and stored with the patient record, a session completion interface may be generated and sent to the first clinician device and/or the second clinician device with an indication of the annotated images generated during the communication session, as in 706. For example, if a first annotated image that includes a template selected by the clinician and annotations of that template, and a second annotated image that includes a patient image and annotations made to the patient image were generated during the communication session, the first annotated image and the second annotated image may be included in the session completion interface.

The session completion interface may allow the clinician to select which annotated images are to be associated and stored with the patient record, add notes, follow-up items, etc., from the communication session, etc.

Subsequent to sending the session completion interface for presentation by the clinician application executing on the second clinician device and/or the first clinician device, a selection of annotated image(s) is received indicating which of the annotated images are to be associated with the patient record, as in 708.

In some implementations, an indication of the selected annotated images that are associated and stored with the patient record may also be sent to the patient, as in 710. The indication sent to the patient may be for informational purposes, to obtain consent from the patient, to allow the patient to submit notes and/or select/deselect annotated images to associate and store with the patient record of the patient, etc. In other implementations, the patient may not be sent an indication of the annotated images that are being associated and stored with the patient record. In still other examples, the session completion interface may be first sent to the patient for selection of annotated images that the patient would like associated and stored with the patient record and a subsequent notification or indication sent to the clinician.

The annotated images selected by the clinician and/or the patient, are then associated and stored with the patient record of the patient included in the communication session, as in 712.

In some implementations, the example process 700 may periodically determine if additional images and/or other data relating to the session have been received from either the patient and/or the clinician, as in 718. For example, in some implementation the patient may periodically submit additional patient images and/or updates relating to a session purpose of the communication session. Likewise, the clinician may periodically submit updates, images, etc., relating to the session purpose. If it is determined that additional images, data, etc. (collectively "update data"), have been submitted by the clinician and/or the patient, the update data is associated and stored with the patient record, as in 716. In some implementations, the clinician and/or the patient may receive a notification of the update data that has been provided.

If it is determined that no update data has been submitted, or after updating the patient record with the update data, the example process 700 completes, as in 720.

Although the disclosure has been described herein using exemplary techniques, components, and/or processes for implementing the systems and methods of the present disclosure, it should be understood by those skilled in the art that other techniques, components, and/or processes or other combinations and sequences of the techniques, components, and/or processes described herein may be used or performed that achieve the same function(s) and/or result(s) described herein and which are included within the scope of the present disclosure.

It should be understood that, unless otherwise explicitly or implicitly indicated herein, any of the features, characteristics, alternatives or modifications described regarding a particular implementation herein may also be applied, used, or incorporated with any other implementation described herein, and that the drawings and detailed description of the present disclosure are intended to cover all modifications, equivalents and alternatives to the various implementations as defined by the appended claims. Moreover, with respect to the one or more methods or processes of the present disclosure described herein, including but not limited to the flow charts shown in FIGS. 5 through 7 or the transition diagrams shown in FIGS. 1A and 4, orders in which such methods or processes are presented are not intended to be construed as any limitation on the claimed inventions, and any number of the method or process steps or boxes described herein can be combined in any order and/or in parallel to implement the methods or processes described herein. Also, the drawings herein are not drawn to scale.

Conditional language, such as, among others, "can," "could," "might," or "may," unless specifically stated otherwise, or otherwise understood within the context as used, is generally intended to convey in a permissive manner that certain implementations could include, or have the potential to include, but do not mandate or require, certain features, elements and/or steps. In a similar manner, terms such as "include," "including" and "includes" are generally intended to mean "including, but not limited to." Thus, such conditional language is not generally intended to imply that features, elements and/or steps are in any way required for one or more implementations or that one or more implementations necessarily include logic for deciding, with or without user input or prompting, whether these features, elements and/or steps are included or are to be performed in any particular implementation.

The elements of a method, process, or algorithm described in connection with the implementations disclosed herein can be embodied directly in hardware, in a software module stored in one or more memory devices and executed by one or more processors, or in a combination of the two. A software module can reside in RAM, flash memory, ROM, EPROM, EEPROM, registers, a hard disk, a removable disk, a CD-ROM, a DVD-ROM or any other form of non-transitory computer-readable storage medium, media, or physical computer storage known in the art. An example storage medium can be coupled to the processor such that the processor can read information from, and write information to, the storage medium. In the alternative, the storage medium can be integral to the processor. The storage medium can be volatile or nonvolatile. The processor and the storage medium can reside in an ASIC. The ASIC can reside in a user terminal. In the alternative, the processor and the storage medium can reside as discrete components in a user terminal.

Disjunctive language such as the phrase "at least one of X, Y, or Z," or "at least one of X, Y and Z," unless specifically stated otherwise, is otherwise understood with the context as used in general to present that an item, term, etc., may be either X, Y, or Z, or any combination thereof (e.g., X, Y, and/or Z). Thus, such disjunctive language is not generally intended to, and should not, imply that certain implementations require at least one of X, at least one of Y, or at least one of Z to each be present.

Unless otherwise explicitly stated, articles such as "a" or "an" should generally be interpreted to include one or more described items. Accordingly, phrases such as "a device configured to" are intended to include one or more recited devices. Such one or more recited devices can also be collectively configured to carry out the stated recitations. For example, "a processor configured to carry out recitations A, B and C" can include a first processor configured to carry out recitation A working in conjunction with a second processor configured to carry out recitations B and C.

Language of degree used herein, such as the terms "about," "approximately," "generally," "nearly" or "substantially" as used herein, represent a value, amount, or characteristic close to the stated value, amount, or characteristic that still performs a desired function or achieves a desired result. For example, the terms "about," "approximately," "generally," "nearly" or "substantially" may refer to an amount that is within less than 10% of, within less than 5% of, within less than 1% of, within less than 0.1% of, and within less than 0.01% of the stated amount.

Although the invention has been described and illustrated with respect to illustrative implementations thereof, the foregoing and various other additions and omissions may be made therein and thereto without departing from the spirit and scope of the present disclosure.

What is claimed is:

1. A computer-implemented method, comprising:
   establishing a communication session between a patient device and both a first clinician device and a second clinician device, wherein the communication session includes:
      a first connection between the first clinician device and the patient device, wherein the first connection includes at least one of a video connection or an audio connection; and
      a data connection between the second clinician device and the patient device, wherein the data connection is configured to exchange content other than the video connection or the audio connection such that the video connection and the audio connection are not presented or played on the second clinician device;
   during the communication session:
      maintaining, via the first connection, at least one of a video communication or an audio communication between the first clinician device and the patient device;
      detecting an input at the second clinician device;
      in response to detecting the input at the second clinician device, sending for presentation on the second clinician device, a template;
      receiving, at the second clinician device, an annotation with respect to the template;
      determining that the annotation of the template is complete;
      generating, in response to determining that the annotation is complete, an annotated image that includes the template and the annotation; and
      sending the annotated image, via the data connection, from the second clinician device to the patient device for presentation on the patient device, without sending the annotated image to the first clinician device.

2. The computer-implemented method of claim 1, wherein establishing the communication session includes:
   establishing, using a signaling channel, the first connection between the first clinician device and the patient device, wherein the first connection includes the at least one of the video connection or the audio connection;
   using the signaling channel as the data connection between the second clinician device and the patient device.

3. The computer-implemented method of claim 1, further comprising:
   during the communication session:
      receiving a patient image from the patient device;
      sending the patient image to the second clinician device for presentation at the second clinician device, without sending the patient image to the first clinician device;
      receiving, at the second clinician device, a second annotation with respect to the patient image;
      determining that the second annotation of the patient image is complete;
      generating, in response to determining that the second annotation is complete, a second annotated image that includes a representation of the patient image and the second annotation; and
      sending the second annotated image, via the data connection, from the second clinician device to the patient device for presentation on the patient device, without sending the annotated image to the first clinician device.

4. The computer-implemented method of claim 1, wherein:
   at least one of a video of a patient sent from the patient device to the first clinician device or an audio sent from the patient device to the first clinician device remains unobstructed during annotation of the template; and
   the video of the patient or the audio is not sent to the second clinician device.

5. A system, comprising:
   a first clinician device application executing on a first clinician device;
   a second clinician device application executing on a second clinician device;
   a patient device application executing on a patient device; and
   a communication service executing on a remote computing resource, the communication service operable to at least:
      establish a communication session that includes:
         at least one of a video connection or an audio connection between the first clinician device application and the patient device application; and
         a data connection between the second clinician device application and the patient device application, wherein the data connection is configured to exchange content other than the video connection or the audio connection such that the video connection and the audio connection are not presented or played on the second clinician device; and
      wherein, during the communication session, and without disrupting the video connection or the audio connection:
         a clinician, through use of the second clinician device application executing on the second clinician device, annotates at least one of a template or a patient image presented on a second clinician device display;
         an annotated image of the annotation and the at least one of the template or the patient image is generated;
         the annotated image is sent from the second clinician device application to the patient device application for presentation on a patient device display; and
         the annotated image is not sent to the first clinician device application.

6. The system of claim 5, wherein the communication service is operable to at least:
   determine a session purpose corresponding to the communication session;
   determine at least one template corresponding to the session purpose; and
   send to the second clinician device application, for presentation on the second clinician device display, the at least one template.

7. The system of claim 6, wherein the communication service is operable to determine the session purpose based at least in part on one or more of:
   a first indication of the session purpose received from the patient device application;
   a second indication of the session purpose received from the first clinician device application;
   a third indication of the session purpose received from the second clinician device application; or
   a determination of the session purpose based on a substance of the communication session.

8. The system of claim 7, wherein the substance of the communication session is determined based on one or more of audio data of the communication session, video data of the communication session, a selected template used in the communication session, a search term input to one or more of the patient device application, the first clinician device application, or the second clinician device application, a patient history, or annotations received by the second clinician device application.

9. The system of claim 5, wherein the second clinician device application is further operable to at least:
present, on the second clinician device display, the at least one of the patient image or the template;
receive the annotation input by the clinician via the second clinician device display;
determine that input of the annotation is complete;
in response to determination that the input of the annotation is complete, generate the annotated image of the annotation and the at least one of the template or the patient image; and
send the annotated image from the second clinician device application for presentation on the patient device display.

10. The system of claim 9, wherein the second clinician device application is further operable to at least:
determine that input of the annotation is complete based on one or more of:
a completion indication received from the clinician, or
a time duration elapsing without additional annotation input on the second clinician device display.

11. The system of claim 5, wherein a video of a patient sent from the patient device application to the first clinician device application and displayed on a first clinician device display remains unobstructed during the communication session.

12. The system of claim 5, wherein the first clinician device application is further operable to at least:
present a patient record of a patient; and
present at least one of a real-time or near real-time video of the patient received from the patient device application or a real-time or near real-time audio received from the patient device application.

13. The system of claim 5, wherein the communication service is further operable to at least:
determine a completion of the communication session;
send for presentation, by at least one of the first clinician device application or the second clinician device application, a session completion interface that includes, at least, the annotated image, and a confirmation request that the annotated image is to be associated with a patient record of a patient using the patient device application;
receive from the first clinician device application or the second clinician device application, a confirmation that the annotated image is to be associated with the patient record;
in response to receiving the confirmation:
store the annotated image in a data store; and
generate an association between the patient record and the stored annotated image.

14. The system of claim 5, wherein the communication service is further operable to at least:
determine a completion of the communication session;
send, for presentation by the patient device application, a session completion interface that includes, at least, the annotated image, and an indication that the annotated image is being associated with a patient record of a patient using the patient device application;
store the annotated image in a data store; and
generate an association between the patient record and the stored annotated image.

15. A method of a multi-channel communication session, comprising:
establishing a first connection between a first clinician device at a first location and a patient device at a second location that is different than the first location;
establishing, concurrent with the first connection, a second connection between a second clinician device at the first location and the patient device;
maintaining at least one of a video communication or an audio communication, via the first connection, between the first clinician device and the patient device, wherein the second connection is configured to exchange content other than the video communication or the audio communication such that the video communication and the audio communication are not presented or played on the second clinician device;
receiving, at the second clinician device and during the at least one of the video communication or the audio communication, an annotation of content presented on a second clinician device display; and
sending, from the second clinician device to the patient device, an annotated image that includes at least the annotation, wherein the annotated image is sent via the second connection and without the annotated image being sent to the first clinician device.

16. The method of claim 15, further comprising:
sending, from the patient device to the second clinician device, via the second connection and without sending to the first clinician device, a patient image generated by the patient device; and
wherein the patient image is included in the content.

17. The method of claim 15, further comprising:
determining a template corresponding to a session purpose of the multi-channel communication session; and
wherein the template is included in the content.

18. The method of claim 17, wherein determining a template includes one or more of:
receiving, from the patient device, a first indication of the session purpose;
receiving, from the first clinician device, a second indication of the session purpose;
receiving, from the second clinician device, a third indication of the session purpose; or determining the session purpose based on a substance of the multi-channel communication session.

19. The method of claim 15, further comprising:
determining a completion of the multi-channel communication session;
presenting, on at least one of a first clinician device display or the second clinician device display, a session completion interface that includes, at least, the annotated image and a confirmation request that the annotated image is to be associated with a patient record of a patient using the patient device;
storing the annotated image in a data store; and
generating an association between the patient record and the annotated image.

20. The method of claim 15, further comprising:
determining a completion of the multi-channel communication session;
presenting, on a patient device display of the patient device, a session completion interface that includes, at least, the annotated image, and an indication that the annotated image is being associated with a patient record of a patient using the patient device;

storing the annotated image in a data store; and generating an association between the patient record and the annotated image.

21. The computer-implemented method of claim 1, wherein both the first clinician device and the second clinician device are associated with a same clinician.

* * * * *